(12) United States Patent
Bitar (10) Patent No.: US 11,638,588 B2
(45) Date of Patent: May 2, 2023

(54) RADIAL ARTERY SHEATH ASSEMBLY

(71) Applicant: Fahed Bitar, Sierra Madre, CA (US)

(72) Inventor: Fahed Bitar, Sierra Madre, CA (US)

( * ) Notice: Subject to any disclaimer, the term of this patent is extended or adjusted under 35 U.S.C. 154(b) by 187 days.

(21) Appl. No.: 17/346,787

(22) Filed: Jun. 14, 2021

(65) Prior Publication Data

US 2022/0395280 A1 Dec. 15, 2022

(51) Int. Cl.
*A61B 17/132* (2006.01)
*A61B 17/135* (2006.01)
*A61B 17/12* (2006.01)

(52) U.S. Cl.
CPC ........ *A61B 17/1322* (2013.01); *A61B 17/135* (2013.01); *A61B 2017/12004* (2013.01)

(58) Field of Classification Search
CPC .............. A61B 17/132; A61B 17/1322; A61B 17/1325; A61B 17/135; A61B 2017/12004
See application file for complete search history.

(56) References Cited

U.S. PATENT DOCUMENTS

| | | | | |
|---|---|---|---|---|
| 3,765,421 A | * | 10/1973 | Poprik | A61M 25/02 604/179 |
| 4,088,136 A | * | 5/1978 | Hasslinger | A61M 25/02 604/179 |
| 4,480,639 A | * | 11/1984 | Peterson | A61M 25/02 604/179 |
| 4,896,465 A | * | 1/1990 | Rhodes | A61M 5/1418 451/523 |
| 5,084,026 A | * | 1/1992 | Shapiro | A61M 25/02 604/179 |
| 5,578,013 A | * | 11/1996 | Bierman | A61M 25/02 604/174 |
| 5,601,597 A | | 2/1997 | Arrowood | |
| 6,471,676 B1 | * | 10/2002 | DeLegge | A61M 25/02 604/175 |
| 6,663,653 B2 | | 12/2003 | Akerfeldt | |
| 8,152,776 B2 | | 4/2012 | McCluskey | |
| 8,657,850 B2 | | 2/2014 | McNeese | |
| 8,834,425 B2 | * | 9/2014 | Bracken | A61L 24/0031 604/179 |
| 9,089,335 B2 | * | 7/2015 | Okamura | A61M 25/02 |
| 9,763,670 B2 | | 9/2017 | Atthoff | |
| D817,486 S | | 5/2018 | Corato | |
| 10,213,212 B2 | | 2/2019 | Pancholy | |
| 11,134,957 B2 | * | 10/2021 | Harding | A61B 17/135 |
| 11,284,905 B2 | * | 3/2022 | Kiemeneij | A61M 39/06 |

(Continued)

FOREIGN PATENT DOCUMENTS

WO WO2011090429 7/2011

*Primary Examiner* — Ryan J. Severson (57) ABSTRACT

A radial artery sheath assembly includes a cuff that is wearable around a patient's wrist and a receiver is integrated into the cuff. The cuff is inflatable to compress an incision in the patient's wrist to achieve homeostasis for stopping bleeding. A ring is removably attachable to the cuff and a radial sheath is extendable through the ring to retain the radial sheath in the incision in the user's wrist when the ring is attached to the cuff. The ring is inflatable for compressing the radial sheath in the ring to inhibit the radial sheath from being removed from the incision. A lock is coupled to the ring and the lock releasably engages the receiver in the cuff for attaching the ring to the cuff.

9 Claims, 5 Drawing Sheets (56) References Cited

U.S. PATENT DOCUMENTS

| | | | | |
|---|---|---|---|---|
| 2003/0055453 | A1* | 3/2003 | Akerfeldt | A61B 17/135 606/203 |
| 2009/0281565 | A1* | 11/2009 | McNeese | A61B 17/1325 606/201 |
| 2010/0137806 | A1* | 6/2010 | McCluskey | A61M 5/1418 604/179 |
| 2012/0296369 | A1* | 11/2012 | Atthoff | A61B 17/1322 606/202 |
| 2013/0023734 | A1* | 1/2013 | Okamura | A61M 25/0097 600/227 |
| 2013/0237866 | A1* | 9/2013 | Cohen | A61B 5/02438 600/502 |
| 2017/0135702 | A1* | 5/2017 | Pancholy | A61B 17/135 |
| 2017/0136215 | A1* | 5/2017 | Harders | A61M 25/02 |
| 2019/0015636 | A1* | 1/2019 | Robinson | A61M 25/02 |
| 2019/0069904 | A1* | 3/2019 | Harding | A61B 17/1355 |
| 2019/0133602 | A1* | 5/2019 | Kiemeneij | A61M 39/06 |
| 2019/0344049 | A1* | 11/2019 | Palomar-Moreno | A61M 25/0113 |
| 2022/0047272 | A1* | 2/2022 | Hopkinson | A61B 17/1322 |
| 2022/0395280 | A1* | 12/2022 | Bitar | A61B 17/135 |

\* cited by examiner

RADIAL ARTERY SHEATH ASSEMBLY

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to artery sheath devices and more particularly pertains to a new artery sheath device for securing a radial artery sheath in place during a cardiac catheterization procedure. The device includes an inflatable cuff and an inflatable ring that is releasably attachable to the inflatable cuff. The inflatable ring insertably receives a radial sheath for stabilizing the radial sheath in an incision. Additionally, the inflatable cuff can be positioned over the incision when the radial sheath is removed from the incision.

(2) Description of Related Art Including Information Disclosed Under 37 CFR 1.97 and 1.98

The prior art relates to artery sheath devices including wrist splint device for immobilizing a wrist joint during radial artery catheterization. The prior art discloses a radial artery clamp for compressing an incision in a radial artery to stop bleeding. The prior art discloses a wrist sleeve for securing dialysis tubes. The prior art discloses a radial artery compression sleeve that is inflatable for compressing a puncture wound of a radial artery. The prior art discloses a variety of compression devices for applying compressing to a radial artery incision for stopping bleeding.

BRIEF SUMMARY OF THE INVENTION

An embodiment of the disclosure meets the needs presented above by generally comprising a cuff that is wearable around a patient's wrist and a receiver is integrated into the cuff. The cuff is inflatable to compress an incision in the patient's wrist to achieve homeostasis for stopping bleeding. A ring is removably attachable to the cuff and a radial sheath is extendable through the ring to retain the radial sheath in the incision in the user's wrist when the ring is attached to the cuff. The ring is inflatable for compressing the radial sheath in the ring to inhibit the radial sheath from being removed from the incision. A lock is coupled to the ring and the lock releasably engages the receiver in the cuff for attaching the ring to the cuff.

There has thus been outlined, rather broadly, the more important features of the disclosure in order that the detailed description thereof that follows may be better understood, and in order that the present contribution to the art may be better appreciated.

There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
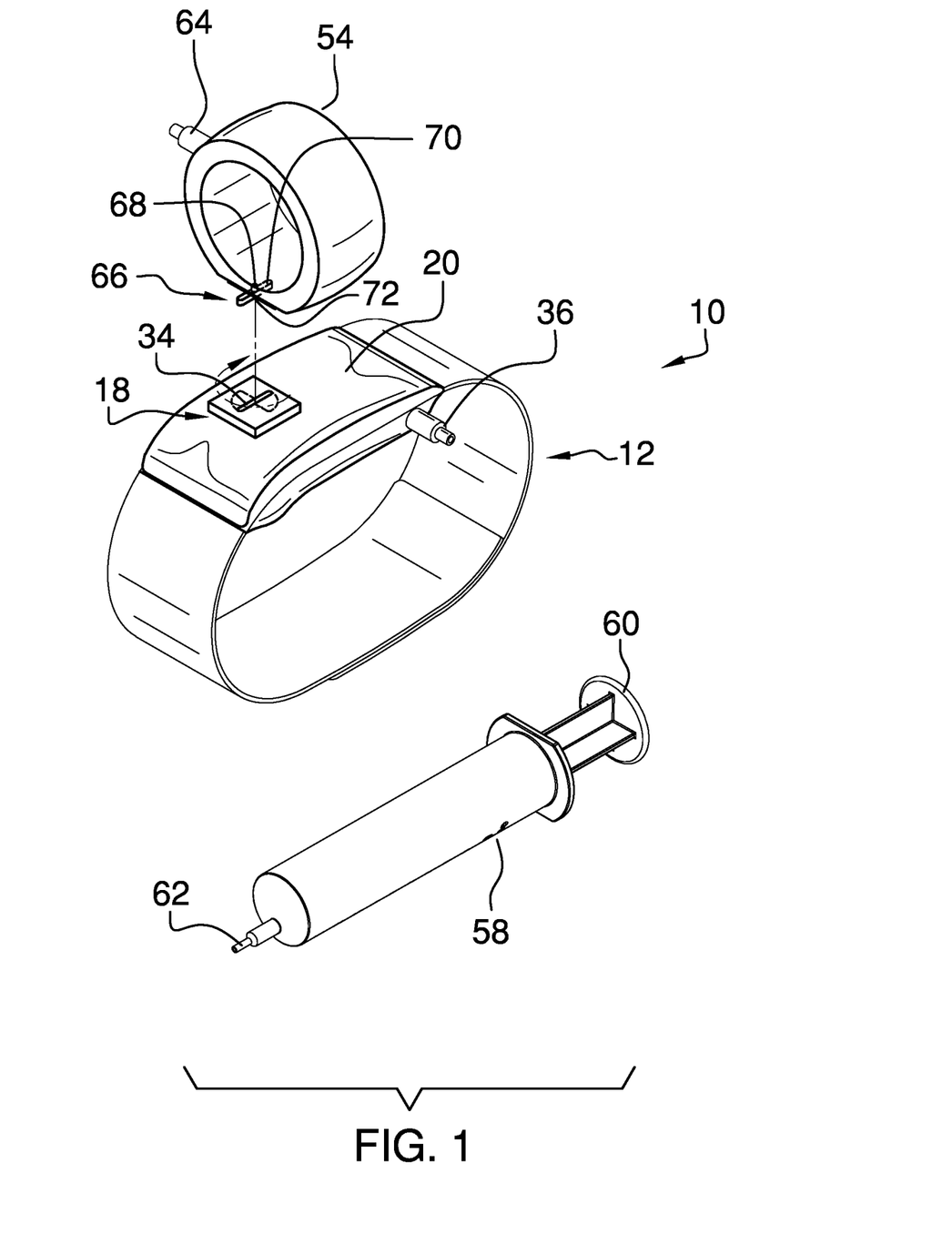
FIG. 1 is a perspective view of a radial artery sheath assembly according to an embodiment of the disclosure.
Figure 2:
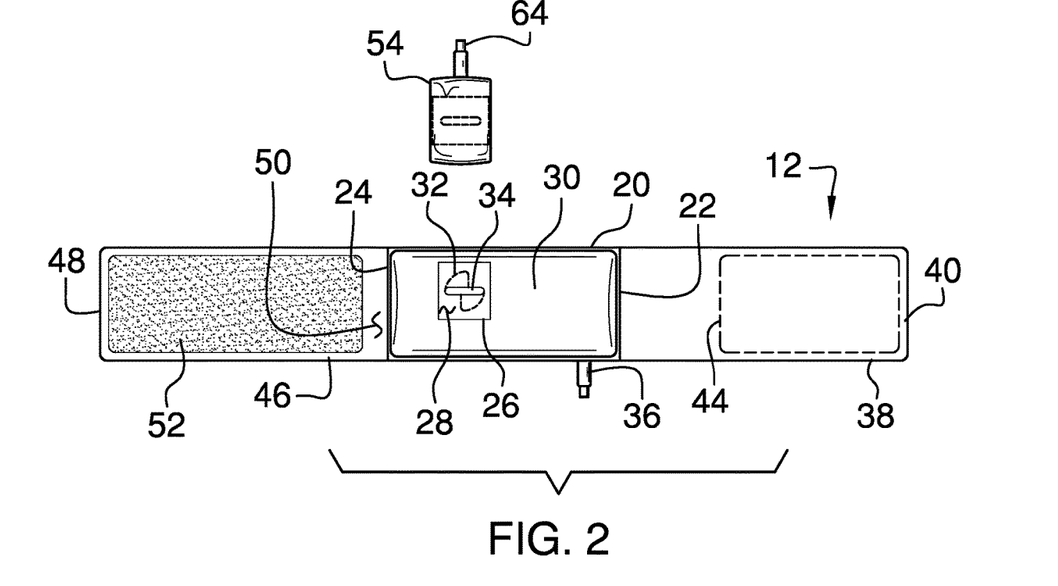
FIG. 2 is a top phantom view of an embodiment of the disclosure.
Figure 3:
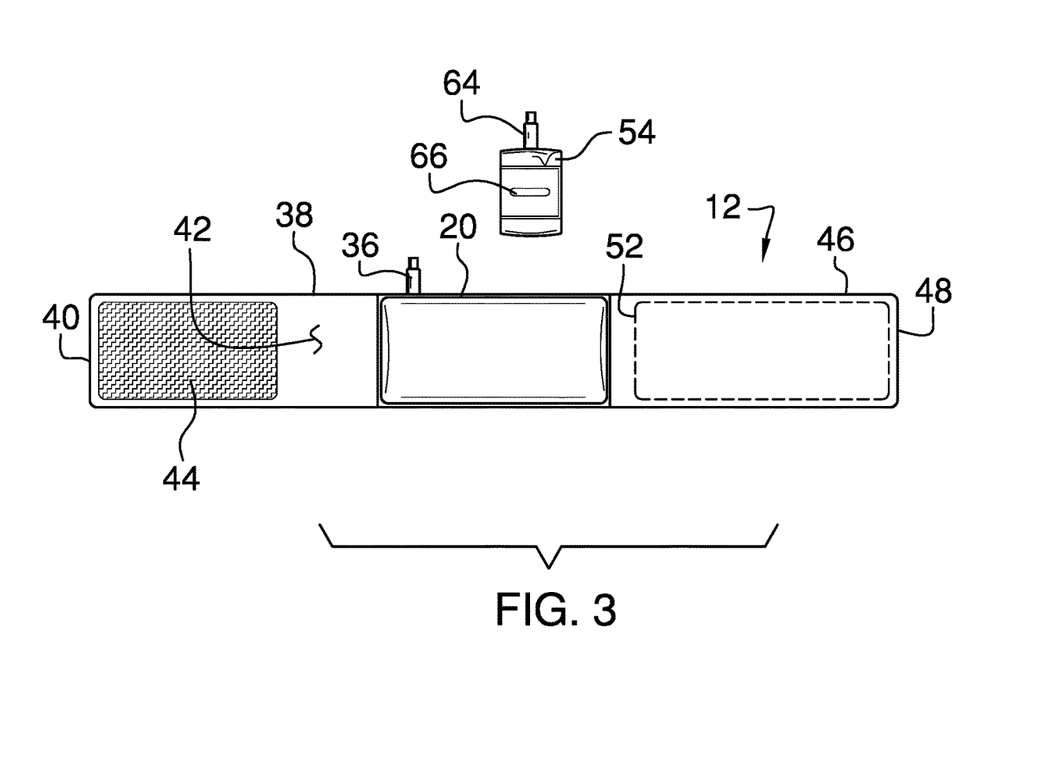
FIG. 3 is a bottom view of an embodiment of the disclosure.
Figure 4:
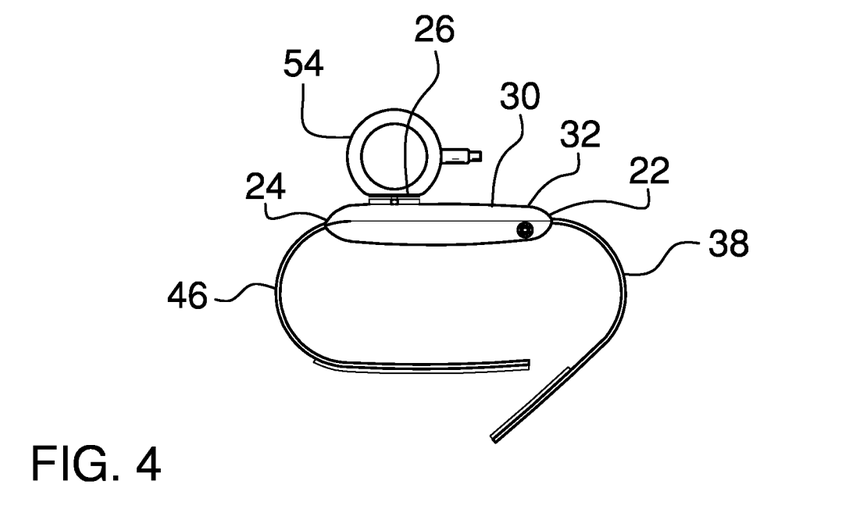
FIG. 4 is a front view of an embodiment of the disclosure.
Figure 5:
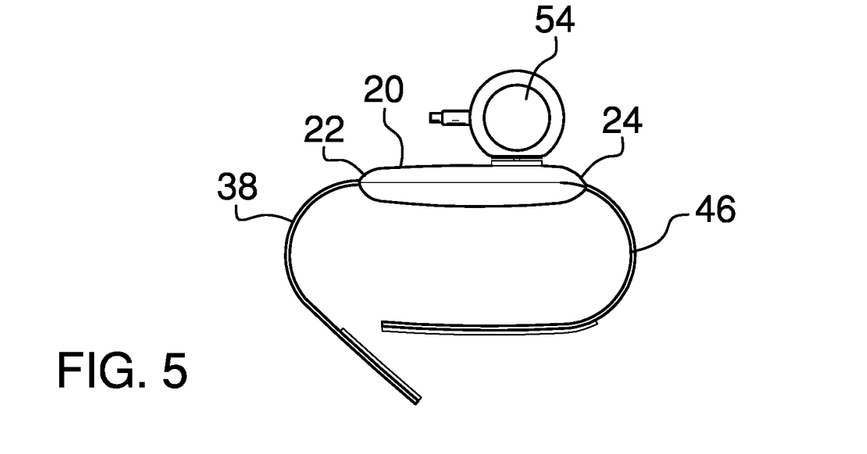
FIG. 5 is a back view of an embodiment of the disclosure.
Figure 6:
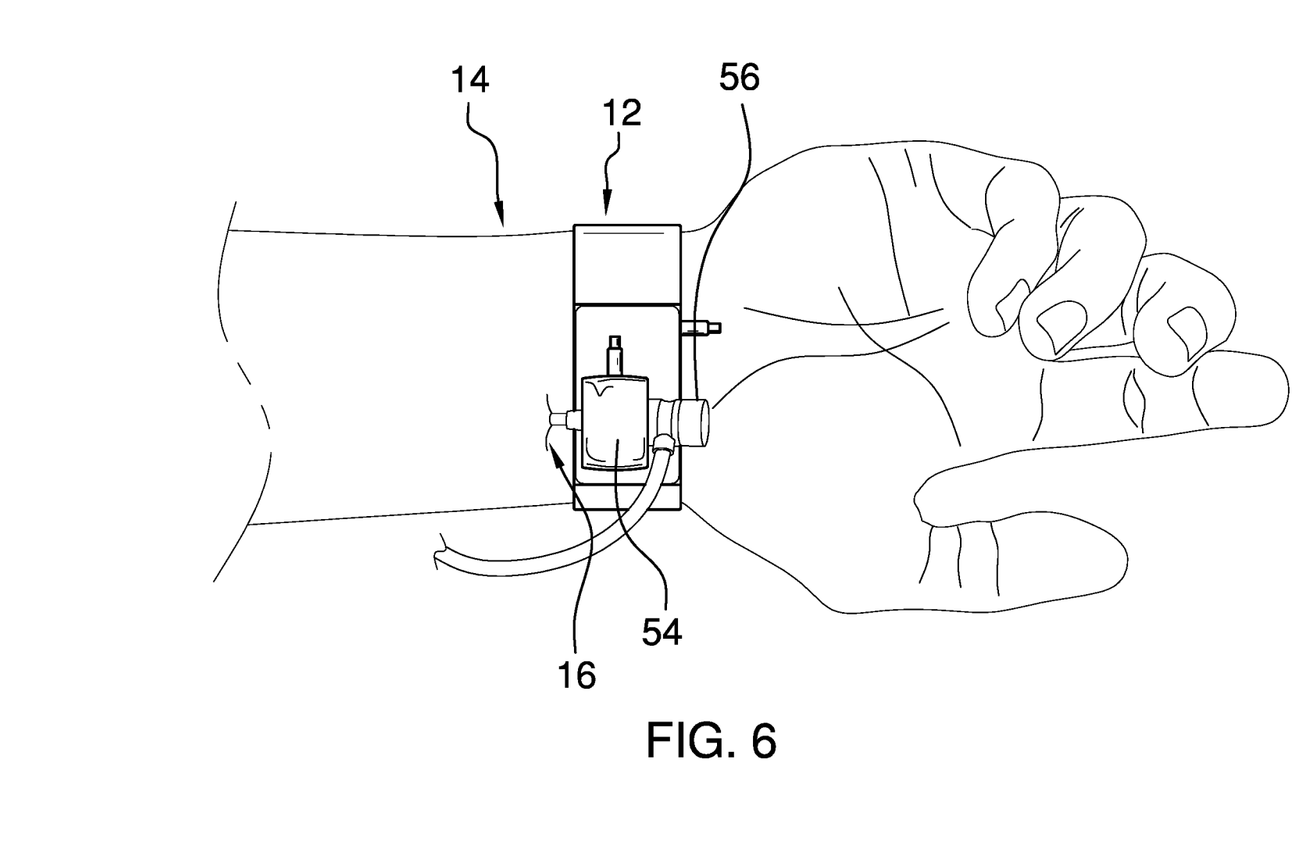
FIG. 6 is a perspective in-use view of an embodiment of the disclosure showing a radial sheath being secured in position.
Figure 7:
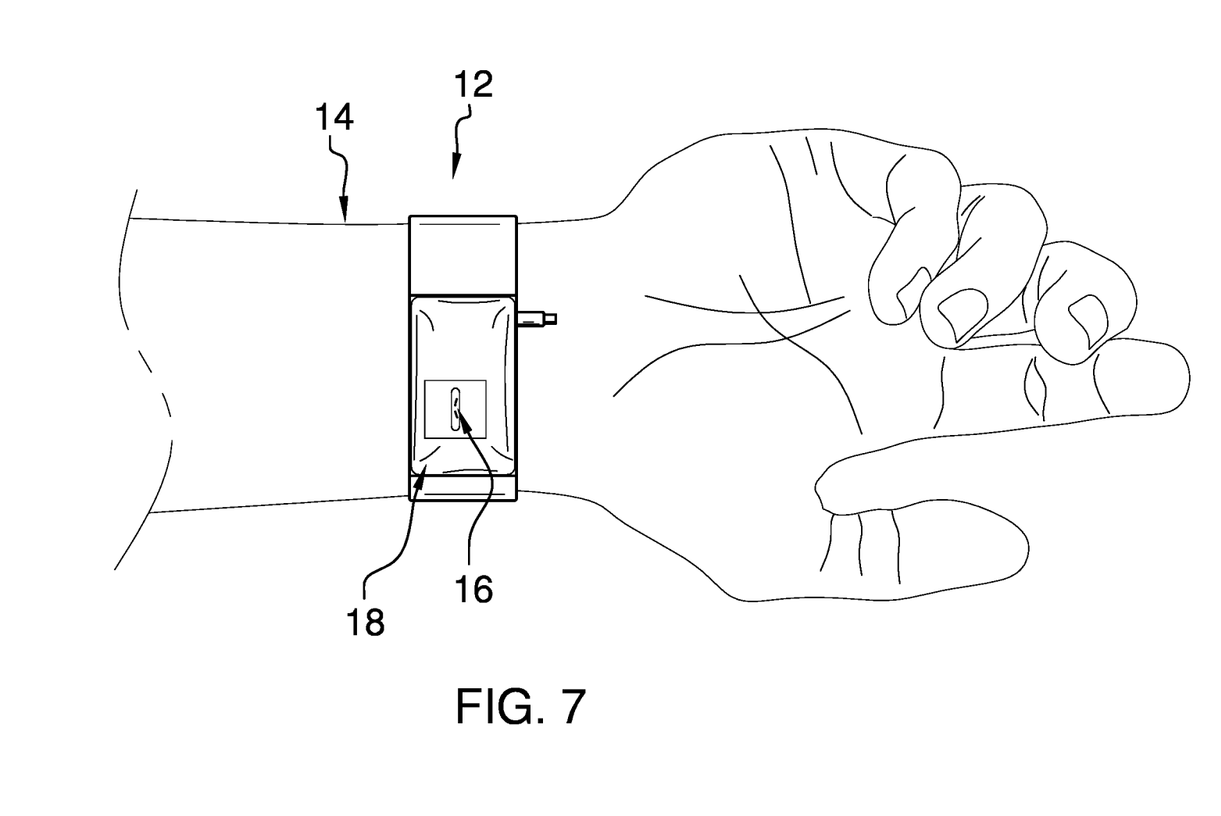
FIG. 7 is a perspective in-use view of an embodiment of the disclosure showing a cuff being positioned over an incision.

With reference now to the drawings, and in particular to FIGS. 1 through 7 thereof, a new artery sheath device embodying the principles and concepts of an embodiment of the disclosure and generally designated by the reference numeral 10 will be described.

As best illustrated in FIGS. 1 through 7, the radial artery sheath assembly 10 generally comprises a cuff 12 that is wearable around a patient's wrist 14 such that the cuff 12 can be positioned proximate the patient's radial artery. The cuff 12 is inflatable to compress an incision 16 in the patient's wrist 14 to achieve homeostasis for stopping bleeding and a receiver 18 is integrated into the cuff 12. The incision 16 may be an incision 16 made to facilitate a radial artery cardiac catheterization. The cuff 12 comprises a bladder 20 that has a first end 22, a second end 24 and a top side 30 extending between the first end 22 and the second end 24. The bladder 20 is elongated between the first end 22 and the second end 24.

A platform 26 is positioned on the top side 30 of the bladder 20 and the platform 26 has an exposed surface 28 with respect to the top side 30. A chamber 32 is integrated into an interior of the platform 26 and the exposed surface 28 has a slot 34 extending into the chamber 32. Thus, the slot 34 and the chamber 32 define the receiver 18 that is integrated into the cuff 12. Additionally, the slot 34 is elongated on the exposed surface 28 to extend along an axis extending between the first end 22 and the second end 24 of the bladder 20.

A first valve 36 is fluidly integrated into the bladder 20 such that the first valve 36 is in fluid communication with an interior of the bladder 20. The first valve 36 is in a normally closed condition to inhibit air from passing into or out of the bladder 20. Conversely, the first valve 36 is actuatable into an open condition to pass air into the bladder 20 for inflating the bladder 20. The first valve 36 may be a normally closed air valve or the like that can be opened with pressurized air.

A first strap 38 is coupled to and extends away from the first end 22 of the bladder 20 and the first strap 38 has a distal end 40 with respect to the first end 22 and a first surface 42. A first mating member 44 is coupled to the first surface 42 of the first strap 38. A second strap 46 is coupled to and extends away from the second end 24 of the bladder 20 and the second strap 46 has a distal end 48 with respect to the second end 24 and a primary surface 50. A second mating member 52 is coupled to the primary surface 50 of the second strap 46. The second mating member 52 is matable to the first mating member 44 such that the first strap 38 and the second strap 46 forms a closed loop for retaining the bladder 20 on the user's wrist 14.

A ring 54 is removably attachable to the cuff 12 and a radial sheath 56 is extended through the ring 54. In this way the radial sheath 56 is retained in the incision 16 in the user's wrist 14 when the ring 54 is attached to the cuff 12. The radial sheath 56 may be an arterial sheath that is commonly employed during a cardiac catheterization procedure. The ring 54 is inflatable for compressing the radial sheath 56 in the ring 54 to inhibit the radial sheath 56 from being removed from the incision 16. In this way a surgeon can insert and remove multiple catheters into the radial sheath 56 without the fear of dislodging the radial sheath 56. Additionally, the radial sheath 56 is inhibited from being dislodged by physical movements of the patient.

A second valve 64 is fluidly integrated into the ring 54 such that the second valve 64 is in fluid communication with an interior of the ring 54. The second valve 64 is in a normally closed condition to inhibit air from passing into or out of the ring 54. Conversely, the second valve 64 is actuatable into an open condition to pass air into the ring 54 for inflating the ring 54. The second valve 64 may comprise a normally closed air valve or the like that can be opened with pressurized air.

A syringe 58 is fluidly attachable to the cuff 12 for inflating the cuff 12 and the syringe 58 is fluidly attachable to the ring 54 for inflating the ring 54. The syringe 58 includes a plunger 60 and an output port 62, and the syringe 58 may have fluid volume of at least 10.0 cubic centimeters. The output port 62 is fluidly attachable to either the first valve 36 or the second valve 64. Moreover, the syringe 58 actuates either the first valve 36 or the second valve 64 into the open condition when the plunger 60 is plunged in the syringe 58 for inflating the bladder 20 or the ring 54.

A lock 66 is coupled to the ring 54 and the lock 66 releasably engages the receiver 18 in the cuff 12 for attaching the ring 54 to the cuff 12. The lock 66 comprises a stem 68 extending downwardly from an outer surface 69 of the ring 54 and a head 70 that is coupled to a distal end 72 of the stem 68. The head 70 is oriented perpendicular to the stem 68 and the head 70 is insertable through the slot 34 in the exposed surface 28 of the platform 26. The ring 54 is rotatable into a locked position such that the head 70 is displaced from the slot 34 having the head 70 being contained in the chamber 32 thereby retaining the head 70 in the chamber 32. Moreover, the ring 54 is oriented such that a circumferential axis of the ring 54 lies on a plane that is coplanar with a circumferential axis of the cuff 12 when the ring 54 is rotated into the locked position. In this way the ring 54 retains the radial sheath 56 in a preferred orientation with respect to the patient's wrist 14.

In use, the cuff 12 is worn around the patient's wrist 14 and the ring 54 is locked into the receiver 18. The cuff 12 is positioned to facilitate the radial sheath 56 to extend through the ring 54. The ring 54 is inflated to secure the radial sheath 56 in the ring 54 during the cardiac catheterization procedure. In this way the surgeon can insert and remove multiple cardiac catheters in the radial sheath 56 without dislodging the radial sheath 56. The radial sheath 56 is removed from the ring 54 and the ring 54 is unlocked from the cuff 12 when the cardiac catheterization procedure is completed. The cuff 12 is positioned over the incision 16 when the radial sheath 56 is removed from the incision 16 and the cuff 12 is inflated. In this way the cuff 12 applies direct pressure to the incision 16 to inhibit bleeding while the incision 16 heals.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A radial artery sheath assembly for securing a radial artery sheath in a patient's arm during a cardiac catheterization procedure, said assembly comprising:
    a cuff being wearable around a patient's wrist wherein said cuff is configured to be positioned proximate the patient's radial artery, said cuff being inflatable wherein said cuff is configured to compress an incision in the patient's wrist to achieve homeostasis for stopping bleeding, said cuff having a receiver being integrated into said cuff;
    a ring being removably attachable to said cuff, said ring having a radial sheath being extended through said ring wherein said ring is configured to retain the radial sheath in the incision in the user's wrist when said ring is attached to said cuff, said ring being inflatable for compressing the radial sheath in said ring wherein said ring is configured to inhibit the radial sheath from being removed from the incision;

a syringe being fluidly attachable to said cuff for inflating said cuff, said syringe being fluidly attachable to said ring for inflating said ring; and a lock being coupled to said ring, said lock releasably engaging said receiver in said cuff for attaching said ring to said cuff.

2. The assembly according to claim 1, wherein said cuff comprises:

a bladder having a first end, a second end and a top side extending between said first end and said second end, said bladder being elongated between said first end and said second end;

a platform being positioned on said top side of said bladder, said platform having an exposed surface with respect to said top side, platform having a chamber being integrated into an interior of said platform, said exposed surface having a slot extending into said chamber such that said slot and said chamber define said receiver being integrated into said cuff, said slot being elongated on said exposed surface to extend along an axis extending between said first end and said second end of said bladder; and a first valve being fluidly integrated into said bladder such that said first valve is in fluid communication with an interior of said bladder, said first valve being in a normally closed condition wherein said first valve is configured to inhibit air from passing into or out of said bladder, said first valve being actuatable into an open condition wherein said first valve is configured to pass air into said bladder for inflating said bladder.

3. The assembly according to claim 2, wherein said cuff comprises:

a first strap being coupled to and extending away from said first end of said bladder, said first strap having a distal end with respect to said first end and a first surface; and a first mating member being coupled to said first surface of said first strap.

4. The assembly according to claim 2, wherein said cuff comprises:

a second strap being coupled to and extending away from said second end of said bladder, said second strap having a distal end with respect to said second end and a primary surface; and a second mating member being coupled to said primary surface of said second strap, said second mating member being matable to said first mating member having said first strap and said second strap forming a closed loop wherein said bladder is configured to be retained on the user's wrist.

5. The assembly according to claim 2, wherein said lock comprises a stem extending downwardly from an outer surface of said ring and a head being coupled to a distal end of said stem, said head being oriented perpendicular to said stem, said head being insertable through said slot in said exposed surface of said platform.

6. The assembly according to claim 5, wherein said ring being rotatable into a locked position such that said head is displaced from said slot having said head being contained in said chamber thereby retaining said head in said chamber, said ring being oriented such that a circumferential axis of said ring lies on a plane being coplanar with a circumferential axis of said cuff when said ring is rotated into said locked position wherein said ring is configured to retain the radial sheath in preferred orientation with respect to the patient's wrist.

7. The assembly according to claim 1, wherein:

said cuff includes a bladder and a first valve being fluidly integrated into said bladder; and said assembly includes a second valve being fluidly integrated into said ring such that said second valve is in fluid communication with an interior of said ring, said second valve being in a normally closed condition wherein said second valve is configured to inhibit air from passing into or out of said ring, said second valve being actuatable into an open condition wherein said second valve is configured to pass air into said ring for inflating said ring.

8. The assembly according to claim 7, wherein said syringe includes a plunger and an output port, said output port being fluidly attachable to either said first valve or said second valve, said syringe actuating either said first valve or said second valve into said open condition when said plunger is plunged in said syringe for inflating said bladder or said ring.

9. A radial artery sheath assembly for securing a radial artery sheath in a patient's arm during a cardiac catheterization procedure, said assembly comprising:

a cuff being wearable around a patient's wrist wherein said cuff is configured to be positioned proximate the patient's radial artery, said cuff being inflatable wherein said cuff is configured to compress an incision in the patient's wrist to achieve homeostasis for stopping bleeding, said cuff having a receiver being integrated into said cuff, said cuff comprising:

a bladder having a first end, a second end and a top side extending between said first end and said second end, said bladder being elongated between said first end and said second end;

a platform being positioned on said top side of said bladder, said platform having an exposed surface with respect to said top side, platform having a chamber being integrated into an interior of said platform, said exposed surface having a slot extending into said chamber such that said slot and said chamber define said receiver being integrated into said cuff, said slot being elongated on said exposed surface to extend along an axis extending between said first end and said second end of said bladder;

a first valve being fluidly integrated into said bladder such that said first valve is in fluid communication with an interior of said bladder, said first valve being in a normally closed condition wherein said first valve is configured to inhibit air from passing into or out of said bladder, said first valve being actuatable into an open condition wherein said first valve is configured to pass air into said bladder for inflating said bladder;

a first strap being coupled to and extending away from said first end of said bladder, said first strap having a distal end with respect to said first end and a first surface;

a first mating member being coupled to said first surface of said first strap;

a second strap being coupled to and extending away from said second end of said bladder, said second strap having a distal end with respect to said second end and a primary surface; and a second mating member being coupled to said primary surface of said second strap, said second mating member being matable to said first mating member having said first strap and said second strap forming a closed loop wherein said bladder is configured to be retained on the user's wrist;

a ring being removably attachable to said cuff, said ring having a radial sheath being extended through said ring wherein said ring is configured to retain the radial sheath in the incision in the user's wrist when said ring is attached to said cuff, said ring being inflatable for compressing the radial sheath in said ring wherein said ring is configured to inhibit the radial sheath from being removed from the incision;

a second valve being fluidly integrated into said ring such that said second valve is in fluid communication with an interior of said ring, said second valve being in a normally closed condition wherein said second valve is configured to inhibit air from passing into or out of said ring, said second valve being actuatable into an open condition wherein said second valve is configured to pass air into said ring for inflating said ring;

a syringe being fluidly attachable to said cuff for inflating said cuff, said syringe being fluidly attachable to said ring for inflating said ring, said syringe including a plunger and an output port, said output port being fluidly attachable to either said first valve or said second valve, said syringe actuating either said first valve or said second valve into said open condition when said plunger is plunged in said syringe for inflating said bladder or said ring; and a lock being coupled to said ring, said lock releasably engaging said receiver in said cuff for attaching said ring to said cuff, said lock comprising a stem extending downwardly from an outer surface of said ring and a head being coupled to a distal end of said stem, said head being oriented perpendicular to said stem, said head being insertable through said slot in said exposed surface of said platform, said ring being rotatable into a locked position such that said head is displaced from said slot having said head being contained in said chamber thereby retaining said head in said chamber, said ring being oriented such that a circumferential axis of said ring lies on a plane being coplanar with a circumferential axis of said cuff when said ring is rotated into said locked position wherein said ring is configured to retain the radial sheath in preferred orientation with respect to the patient's wrist.

* * * * *